(12) United States Patent
Bergmann et al.

(10) Patent No.: US 7,413,850 B2
(45) Date of Patent: Aug. 19, 2008

(54) USES OF CARBAMOYL PHOSPHATE SYNTHETASE FOR THE DIAGNOIS OF INFLAMMATORY DISEASES AND SEPSIS

(75) Inventors: Andreas Bergmann, Berlin (DE); Joachim Struck, Berlin (DE); Monika Uhlein, Berlin (DE)

(73) Assignee: B.R.A.H.M.S. Aktiengesellschaft, Hennigsdorf (DE)

( * ) Notice: Subject to any disclaimer, the term of this patent is extended or adjusted under 35 U.S.C. 154(b) by 102 days.

(21) Appl. No.: 10/511,756

(22) PCT Filed: Apr. 15, 2003

(86) PCT No.: PCT/EP03/03939

§ 371 (c)(1),
(2), (4) Date: May 25, 2005

(87) PCT Pub. No.: WO03/089933

PCT Pub. Date: Oct. 30, 2003

(65) Prior Publication Data

US 2006/0115869 A1 Jun. 1, 2006

(30) Foreign Application Priority Data

Apr. 19, 2002 (EP) .................................. 02008841

(51) Int. Cl.
*C12Q 1/00* (2006.01)
*G01N 33/53* (2006.01)
*G01N 33/563* (2006.01)
*C12P 21/06* (2006.01)
*A61K 49/00* (2006.01)
*A61K 33/43* (2006.01)

(52) U.S. Cl. .............................. 435/4; 435/7.6; 435/7.9; 435/7.1; 435/69.1; 436/512; 424/9.1; 424/94.1

(58) Field of Classification Search ...................... 435/4, 435/7.6, 7.9, 7.1, 69.1; 436/512; 424/9.1, 424/94.1
See application file for complete search history.

(56) References Cited

U.S. PATENT DOCUMENTS

| | | | |
|---|---|---|---|
| 4,822,733 A | 4/1989 | Morrison | |
| 5,512,493 A | 4/1996 | Mathis et al. | |
| 5,639,617 A | 6/1997 | Bohuon | |
| 7,132,246 B2 | 11/2006 | Bergmann et al. | |
| 7,157,081 B2 | 1/2007 | Bergmann et al. | |
| 2004/0180396 A1 | 9/2004 | Bergmann et al. | |
| 2005/0059104 A1 | 3/2005 | Bergmann et al. | |
| 2005/0064506 A1 | 3/2005 | Bergmann et al. | |
| 2005/0074811 A1 | 4/2005 | Bergmann et al. | |
| 2005/0106645 A1 | 5/2005 | Bergmann et al. | |
| 2005/0239150 A1 | 10/2005 | Bergmann et al. | |
| 2006/0029990 A1 | 2/2006 | Bergmann et al. | |
| 2006/0035221 A1 | 2/2006 | Bergmann et al. | |
| 2006/0234295 A1 | 10/2006 | Bergmann et al. | |

FOREIGN PATENT DOCUMENTS

| | | |
|---|---|---|
| EP | 0 656 121 B1 | 3/1998 |
| WO | 00/73322 | 12/2000 |

OTHER PUBLICATIONS

Yin et al. Participation of different cell types in the restitutive response of the rat liver to periportal injury induced by allyl alcohol Journal of Hepatology 1999; 31: 497-507.*
Ozaki et al. Enzyme-Linked Immunosorbent Assay of Carbamoyl phosphate Synthase 1: Plasma Enzyme in Rat Experimental Hepatitis and Clearance. Enzyme protein 1994 95:48:213-221.*
Tabuchi et al (Regulation of Genes for inducible Nitric Oxide Synthase and Urea Cycle Enzymes in Rat Liver in Endotoxin Shock Biochemical and biophysical research communications vol. 268, 221-224 (2000).*
Cerdan et al. (Role of calcium as an inhibitor of carbamoyl phosphate synthetase I Journal of Biological Chemistry 1984, vol. 259, No. 1, p. 323-331.*
Ardawi, M. S. M. "Hepatic Glutamine Metabolism in the Septic Rat," *Clinical Science* (London)., 1992, vol. 82, No. 6, pp. 709-716.
Assicot, M. et al. "High Serum Procalcitonin Concentrations in Patients with Sepsis and Infection," *The Lancet.*, 1993, vol. 341, No. 8844, pp. 515-518.
Beishuizen, A. et al. "Endogenous Mediators in Sepsis and Septic Shock," *Advances in Clinical Chemistry.*, 1999, vol. 33, pp. 55-131.
Gabay, C. et al. "Acute-Phase Proteins and Other Systemic Responses to Inflammation," *The New England Journal of Medicine.*, 1999, vol. 340, No. 6, pp. 448-454.
Ghillani, P. et al. "Monoclonal Antipeptide Antibodies as Tools to Dissect Closely Related Gene Products," *Journal of Immunology.*, 1988, vol. 141, No. 9, pp. 3156-3163.
Ghillani, P. et al. "Identification and Measurement of Calcitonin Precursors in Serum of Patients with Malignant Diseases," *Cancer Research,.* 1989, vol. 49, pp. 6845-6851.
Klose, J. "Two-dimensional Electrophoresis of Proteins: An Updated Protocol and Implications for a Functional Analysis of the Genome," *Electrophoresis.*, 1995, vol. 15, pp. 1034-1059.

(Continued)

Primary Examiner—Robert B. Mondesi
Assistant Examiner—Kagnew Gebreyesus
(74) *Attorney, Agent, or Firm*—Heslin Rothenberg Farley & Mesiti P.C.; Charles E. Bell

(57) ABSTRACT

Use of carbamoyl phosphate synthetase 1 (CPS 1) and/or of fragments of the N-terminal part of CPS 1 from body fluids or body tissues as marker peptides for the diagnosis and for the prognosis and the monitoring of inflammations and infections, including sepsis, and of liver failure as part of multiorgan failure or for determinations in connection with inflammatory and other liver diseases.

12 Claims, 4 Drawing Sheets

OTHER PUBLICATIONS

Figure 1:
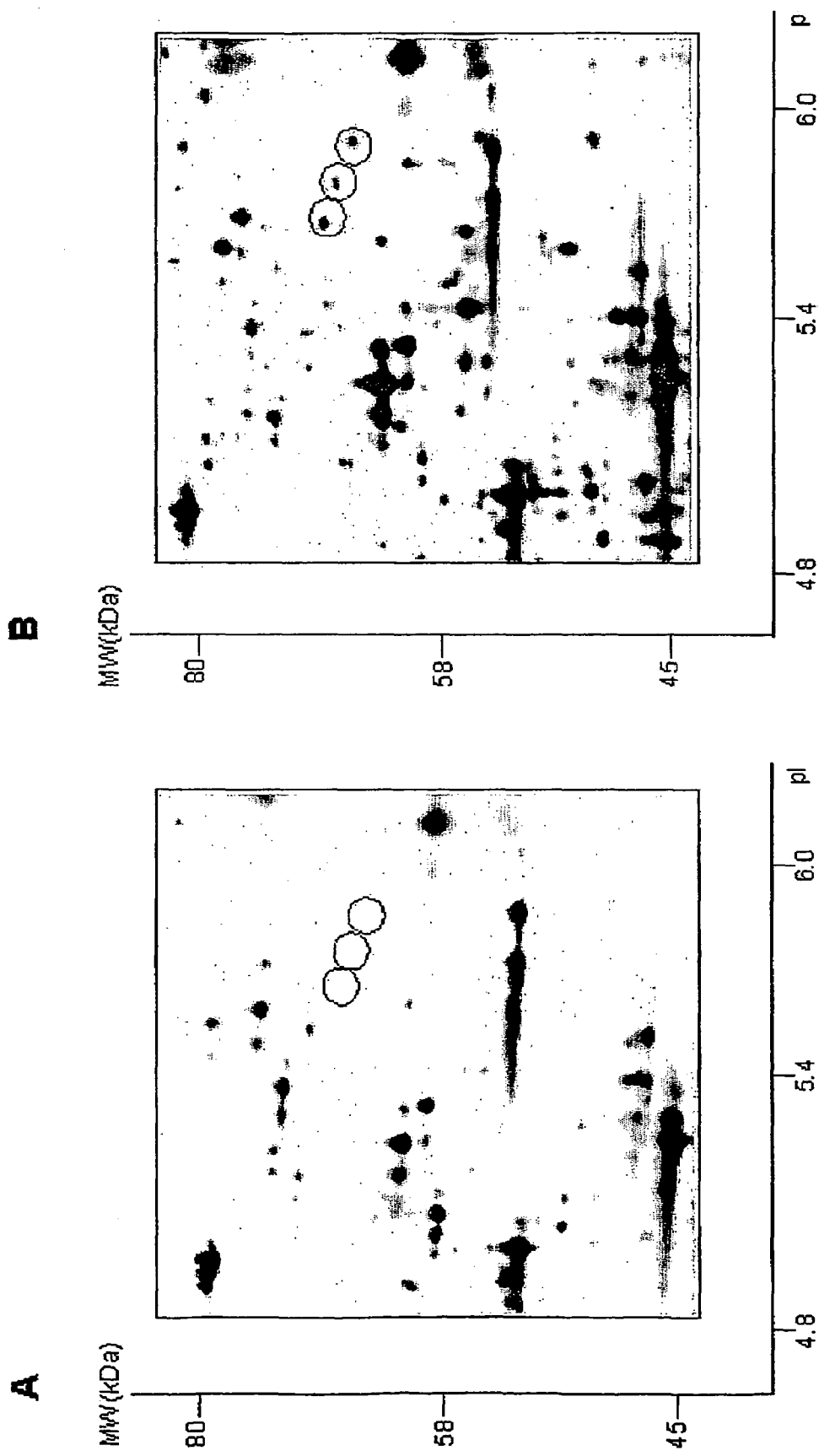

Linger et al. "Reverse Transcriptase Motifs in the Catalytic Subunit of Telomerase," *Science.*, 1997, vol. 276, pp. 561-567.

Mann et al. "Use of Mass Spectrometry-Derived Data to Annotate Nucleotide and Protein Sequence Databases," *Biochemical Sciences.*, 2001, vol. 26, No. 1, pp. 54-61.

Neubauer et al. "Mass Spectrometry and EST-Database Searching Allows Characterization of the Multi-Protein Spliceosome Complex," *Nature Genetics.*, 1998, vol. 20, 46-50.

Neuhoff, V. et al. "Improved Staining of Proteins in Polyacrylamide Gels Including Isoelectric Focusing Gels with Clear Background at Nanogram Sensitivity using Coomassie Brilliant Blue G-250 and R-250," *Electrophoresis.*, 1988, vol. 9, pp. 255-262.

Nielsen, S. et al. "Acute Systemic and Local Inflammation Decreases Hepatic Expressions of Urea Cycle Enzymes," *Journal of Hepatology.*, 2000, vol. 32 (Suppl. 2), pp. 161.

Otto, A. et al. "Identification of Human Myocardial Proteins Separated by Two-Dimensional Electrophoresis using an Effective Sample Preparation for Mass Spectrometry," *Electrophoresis.*, 1996, vol. 17, pp. 1643-1650.

Ozaki, M. et al. "Enzyme-Linked Immunosorbent Assay of Carbamoylphosphate Synthetase I: Plasma Enzyme in Rat Experimental Hepatitis and its Clearance," *Enzyme Protein.*, 1994, vol. 48, No. 4, pp. 213-221.

Redl, H. et al. "Non-Human Primate Models of Sepsis," *Sepsis.*, 1998, vol. 2, pp. 243-253.

Redl, H. et al. "Procalcitonin Release Patterns in a Baboon Model of Trauma and Sepsis: Relationship to Cytokines and Neopterin," *Crit Care Med.*, 2000, vol. 28, No. 11, pp. 3659-3663.

Schimke, R. "Adaptive Characteristics of Urea Cycle Enzymes in the Rat," *Journal of Biological Chemistry.*, 1962, vol. 237, No. 2, pp. 459-468.

Szondy, Z. et al. "Effect of Polyamines on the Carbamoylphosphate Synthetase Activity of Cad Protein," *Database: BioSciences Information Service.*, 1989, vol. 24, pp. 107-118.

Tabuchi, S. et al. "Regulation of Genes for Inducible Nitric Oxide Synthase and Urea Cycle Enzymes in Rat Liver in Endotoxin Shock," *Ciochemical and Ciophysical Research Communications.*, 2000, vol. 268, No. 1, pp. 221-224.

Tygstrup, N. et al. "Expression of Liver Functions Following Sub-Lethal and Non-Lethal Doses of Allyl Alcohol and Acetaminophen in the Rat," *Journal of Hepatology.*, 1997, vol. 27, No. 1, pp. 156-162.

Yin, L. et al. "Participation of Different Cell Types in the Restitutive Response ot the Rat Liver to Periportal Injury Induced by Allyl Alcohol," *Journal of Hepatology.*, 1999, vol. 31, No. 3, pp. 497-507.

Office Action dated Sep. 24, 2007 in co-pending U.S. Appl. No. 10/496,173.

Office Action dated Sep. 4, 2007 in co-pending U.S. Appl. No. 10/496,096.

Notice of Allowability in co-pending U.S. Appl. No. 10/511,758.

Office Action dated Jun. 27, 2007 in co-pending U.S. Appl. No. 10/496,250.

Office Action dated Jan. 7, 2008 in co-pending U.S. Appl. No. 10/497,679.

Office Action dated Jan. 29, 2008 in co-pending U.S. Appl. No. 10/516,618.

* cited by examiner

USES OF CARBAMOYL PHOSPHATE SYNTHETASE FOR THE DIAGNOIS OF INFLAMMATORY DISEASES AND SEPSIS

CROSS REFERENCE TO RELATED APPLICATION

This application is the National Phase application of International Application No. PCT/EP2003/003939, filed Apr. 15, 2003, which designates the United States. This application, in its entirety, is incorporated herein by reference.

The present invention relates to uses of the enzyme carbamoyl phosphate synthetase 1 (E.C. 6.3.4.16, always abbreviated to CPS 1) and novel fragments thereof for the medical diagnosis of inflammatory diseases and sepsis. It is based on the detection for the first time of the occurrence of fragments of CPS 1 in liver tissue of primates in which a sepsis or systemic inflammation had been induced experimentally by toxin administration, and on the subsequent detection of greatly increased concentrations of CPS 1 in the circulation of patients suffering from sepsis.

The present invention has its origin in intensive research work by the Applicant in relation to further improvements of the diagnosis and therapy of inflammations and infections, in particular of inflammations of infectious aetiology and sepsis.

Inflammations are defined very generally as certain physiological reactions of an organism to different types of external effects, such as, for example, injuries, burns, allergens, infections by microorganisms, such as bacteria and fungi and viruses, to foreign tissues which trigger rejection reactions, or to certain endogenous states of the body which trigger inflammation, for example in autoimmune diseases and cancer. Inflammations may occur as harmless, localized reactions of the body but are also typical features of numerous serious chronic and acute diseases of individual tissues, organs, organ parts and tissue parts.

Local inflammations are generally part of the healthy immune response of the body to harmful effects, and hence part of the life-preserving defence mechanism of the organism. However, if inflammations are part of a misdirected response of the body to certain endogenous processes, such as, for example, in autoimmune diseases, and/or are of a chronic nature, or if they reach systemic extents, as in the case of systemic inflammatory response syndrome (SIRS) or in a severe sepsis caused by infection, the physiological processes typical of inflammatory reactions go out of control and become the actual, frequently life-threatening pathological process.

It is now known that the origin and the course of inflammatory processes are controlled by a considerable number of substances which are predominantly of a protein or peptide nature or are accompanied by the occurrence of certain biomolecules for a more or less limited time. The endogenous substances involved in inflammatory reactions include in particular those which can be assigned to the cytokines, mediators, vasoactive substances, acute phase proteins and/or hormonal regulators. The inflammatory reaction is a complex physiological reaction in which both endogenous substances activating the inflammatory process (e.g. TNF-α) and deactivating substances (e.g. interleukin-10) are involved.

In systemic inflammations, as in the case of sepsis or of septic shock, the inflammation-specific reaction cascades spread in an uncontrolled manner over the whole body and become life-threatening in the context of an excessive immune response. Regarding the current knowledge about the occurrence and the possible role of individual groups of endogenous inflammation-specific substances, reference is made, for example, to A. Beishuizen et al., "Endogenous Mediators in Sepsis and Septic Shock", Advances in Clinical Chemistry, Vol. 33, 1999, 55-131; and C. Gabay et al., "Acute Phase Proteins and Other Systemic Responses to Inflammation", The New England Journal of Medicine, Vol. 340, No. 6, 1999, 448-454. Since the understanding of sepsis and related systemic inflammatory diseases, and hence also the recognized definition, have changed in recent years, reference is also made to K. Reinhart et al., "Sepsis und septischer Schock" [Sepsis and Septic Shock], in: Intensiv-medizin, Georg Thieme Verlag, Stuttgart, N.Y., 2001, 756-760, where a modern definition of sepsis is given. In the context of the present Application, the terms sepsis and inflammatory diseases used are based on the definitions as given in the three stated references.

Whereas at least in Europe the systemic bacterial infection detectable by a positive blood culture long characterized the term sepsis, sepsis is now primarily understood as being systemic inflammation which is caused by infection but, as a pathological process, has considerable similarities with systemic inflammations which are triggered by other causes. Said transformation in the understanding of sepsis has resulted in changes in the diagnostic approaches. Thus, the direct detection of bacterial pathogens was replaced or supplemented by complex monitoring of physiological parameters and, more recently, in particular by the detection of certain endogenous substances involved in the sepsis process or in the inflammatory process, i.e. specific "biomarkers".

Of the large number of mediators and acute phase proteins which are known to be involved in an inflammatory process, the ones which are suitable for diagnostic purposes are in particular those whose occurrence is very specific for inflammatory diseases or certain phases of inflammatory diseases, whose concentrations change in a dramatic and diagnostically significant manner and which moreover have the stabilities required for routine determinations and reach high concentration values. For diagnostic purposes, the reliable correlation of pathological process (inflammation, sepsis) with the respective biomarker is of primary importance, without there being any need to know its role in the complex cascade of the endogenous substances involved in the inflammatory process.

An endogenous substance of this type which is particulalry suitable as a sepsis biomarker is procalcitonin. Procalcitonin is a prohormone whose serum concentration reach very high values under the conditions of a systemic inflammation of infectious aetiology (sepsis), whereas it is virtually undetectable in healthy persons. High values of procalcitonin are also reached in a relatively early stage of a sepsis so that the determination of procalcitonin is also suitable for early diagnosis of a sepsis or for early distinguishing of a sepsis caused by infection from severe inflammations which have other causes. The determination of procalcitonin as a sepsis marker is the subject of the publication by M. Assicot et al., "High serum procalcitonin concentrations in patients with sepsis and infection", The Lancet, Vol. 341, No. 8844, 1993, 515-518; and the patents DE 42 27 454 C2 and EP 0 656 121 B1 and U.S. Pat. No. 5,639,617. Reference is hereby made to said patents and to early literature references mentioned in said publication for supplementing the present description.

The availability of the sepsis marker procalcitonin has given considerable impetus to sepsis research, and intensive efforts are now being made to find further biomarkers which can supplement the procalcitonin determination and/or are capable of providing additional information for purposes of fine diagnosis or differential diagnosis. The search for potential novel sepsis biomarkers is, however, complicated by the fact that frequently very little or nothing is known about the exact function or about the exact reasons for the occurrence of certain endogenous substances which are involved in the inflammatory or sepsis process.

The results of the experimental testing of a fruitful purely hypothetical approach to the determination of further potential sepsis markers are to be found in DE 198 47 690 A1 and WO 00/22439. There, it is shown that, in the case of sepsis, not only is the concentration of the prohormone procalcitonin is increased but also significantly increased concentrations can be observed for other substances which have prohormone immunoreactivity. While the phenomenon described is well documented, the causes of the increase in the concentrations of the different corresponding substances in sepsis are still substantially unexplained.

In the present Application, the result of another fruitful, purely experimental approach in the search for further inflammation- or sepsis-specific biomolecules is reported. These experimental investigations, too, originate from the determination of procalcitonin in relation to systemic inflammatory reactions of infectious aetiology. Thus, it had been observed at a very early stage that, in sepsis, the procalcitonin is evidently not formed in the same way as when it is a precursor for the hormone calcitonin.

Thus, high procalcitonin levels were also observed in patients whose thyroid had been removed. The thyroid therefore cannot be the organ in which procalcitonin is formed or secreted during sepsis. In the publications by H. Redl et al., "Procalcitonin release patterns in a baboon model of trauma and sepsis: Relationship to cytokines and neopterin", Crit Care Med 2000, Vol. 28, No. 11, 3659-3663; and H. Redl et al., "Non-Human Primate Models of Sepsis", Sepsis 1998; 2:243-253, the results of experimental investigations which are intended to clarify the formation of procalcitonin in sepsis are reported. In said papers, an artificial sepsis is induced by endotoxin administration to primates (baboons), and the experimentally induced states in which the highest procalcitonin concentrations in the blood are reached are determined. In the context of the present Application, a further development of the experimental animal model described in said paper serves for determining novel endogenous sepsis-specific biomarkers of a peptide or protein nature, the occurrence of which is characteristic of sepsis or certain forms of sepsis and which therefore permit a specific sepsis diagnosis. The primate model was chosen on the basis of the very considerable similarity of the physiology of primates and humans and the high cross-reactivity with many therapeutic and diagnostic human reagents.

Since the endogenous substances formed during inflammations are part of the complex reaction cascade of the body, not only are such substances also of diagnostic interest but attempts are also currently being made, with considerable effort, to intervene therapeutically in the inflammatory process by influencing the origin and/or the concentration of individual substances of this type, in order to stop at as early a stage as possible the spread of the inflammation which is observed, for example, in sepsis. In this context, endogenous substances which can be shown to be involved in the inflammatory process are also to be regarded as potential therapeutic targets In spite of the fairly disappointing results of such therapeutic approaches to date, there is still considerable interest in identifying endogenous biomolecules which have not been described to date in the corresponding context, are as inflammation- or sepsis-specific as possible and, as therapeutic targets, also open up new prospects for success for the therapeutic control of sepsis.

The present invention is based on the fact that, in primates and humans, substantially increased concentrations of the enzyme carbamoyl phosphate synthetase (CPS 1) and fragments thereof can be detected in the circulation in inflammations caused by infection, in particular in contrast to untreated control individuals or healthy persons in whom these are not found, making CPS 1 and its fragments suitable for the diagnosis of inflammation/diagnosis of sepsis.

The uses in diagnosis, which arise owing to the detection for the first time of the occurrence of CPS 1 and its fragments in the experimental simulation of inflammations or sepsis and the detection of substantially increased concentrations of CPS 1 immunoreactivity in sera of persons suffering from sepsis, are claimed in herein.

The present invention also relates to variants of diagnostic methods arising from the new discoveries presented herein.

As mentioned in more detail below in the experimental section, the starting point of the invention was the finding that, after experimental triggering of an artificial sepsis in baboons by endotoxin administration (LPS from *Salmonella Typhimurium*) and working-up of liver tissue of the treated animal by 2D gel electrophoresis, it was possible to find a group of adjacent protein spots identifiable only in the treated animals. The protein products corresponding to the spots and having molar masses (determined by gel electrophoresis) of about 68 kDa, 69 kDa and 70 kDa±3 kDa were isolated from the electrophoresis gel, investigated by mass spectrometry and identified as soluble fragments of CPS 1.

Using an immunoassay which detected said fragments, it was then found that components having the immunoreactivity of these fragments are found in greatly increased concentrations in the circulation of patients suffering from sepsis, these commponents proving, on more exact identification (inter alia, isolation and molecular weight determination), to be predominantly the complete or at least substantially complete enzyme CPS 1.

In the mass spectrometric analysis of three protein spots isolated from the gel, which as such have a relatively low intensity, by tandem mass spectrometry, short, partly identical partial peptides ("tags"), which occurred in identical form in the sequence of human CPS 1 (SEQ ID NO:6), were identified from all three protein spots, the peptides specifically identified including amino acid sequences from the N-terminal region of the CPS 1 amino acids up to position 624 of CPS 1 (SEQ ID NO:6).

On the basis of the identity of the identified mass spectrometric fragments with partial sequences from the N-terminal part of CPS 1, the identification of the protein spots investigated have to be regarded unambiguously as CPS 1 fragments according to recognized criteria.

The identification of the proteins found only after triggering of sepsis or of inflammation in baboon liver tissue as fragments from the N-terminal part of CPS 1 is of considerable scientific, diagnostic and therapeutic interest.

The subsequent finding that greatly increased concentrations of one or possibly several species having the immunoreactivity of the CPS 1 fragments identified were observed in the circulation of human patients suffering from sepsis, but which fragments prove to be complete, or at least substantially complete, enzyme CPS 1 which can optionally also be present in a particular solubilized form, considerably increased the value of the first finding described.

CPS 1 and CPS 1 fragments have to date played no practical role in medical diagnostics. The enzyme CPS 1 (E.C.

6.3.4.16) itself has, however, long been well known. It catalyzes the conversion of ammonia, bicarbonate and 2 ATP with formation of carbamoyl phosphate in the first step of the urea cycle. It also plays a role in the biosynthesis of arginine, which in turn is a substrate for the biosynthesis of NO, for example in an endotoxin shock (cf. Shoko Tabuchi et al., Regulation of Genes for Inducible Nitric Oxide Synthase and Urea Cycle Enzymes in Rat Liver in Endotoxin Shock, Biochemical and Biophysical Research Communications 268, 221-224 (2000)). CPS 1 should be distinguished from the cytosolic enzyme CPS 2 (E.C. 2.7.2.5.), which likewise plays a role in the urea cycle but processes the substrate glutamine. It is known that CPS 1 is localized in mitochondria and occurs in liver tissue in this form in large amounts (it accounts for 2-6% of the total liver protein). Its amino acid sequence (SEQ ID NO:6) and genetic localization have long been known (cf. Haraguchi Y. et al., Cloning and sequence of a cDNA encoding human carbamoyl phosphate synthetase I: molecular analysis of hyperammonemia, Gene November 1991, 1; 107 (2): 335-340). Regarding its physiological role, reference may be made to review articles such as, for example, H. M. Holder et al., Carbamoyl phosphate synthetase: an amazing biochemical odyssey from substrate to product, CMLS, Cell. Mol. Life Sic. 56 (1999) 507-522, and the literature referred to therein, and the introduction to the publication by Mikiko Ozaki et al., Enzyme-Linked Immunosorbent Assay of Carbamoyl phosphate Synthetase I: Plasma Enzyme in Rat Experimental Hepatitis and Its Clearance, Enzyme Protein 1994, 95:48:213-221.

According to Shoko Tabuchi et al., loc. cit., no increase in the enzyme (protein) is observed in rat livers in the case of an artificial endotoxin shock (LPS). According to Li Yin et al., Participation of different cell types in the restitutive response of the rat liver to periportal injury induced by allyl alcohol, Journal of Hepatology 1999, 31:497-507, an increase of CPS 1 expression can be observed in the case of liver damage by allyl alcohol on histological investigation after three days in all hepatocytes.

It was furthermore found that, with acute hepatitis experimentally induced by administration of galactosamine in the rat model, a greatly increased immunological CPS 1 activity is present in the rat plasma (detected by means of an ELISA with anti-rat CPS 1 IgG from rabbit) in particular 24-48 h after the treatment with the hepatitis-inducing galactosamine. In rat plasma, CPS 1 fragments having molar masses of about 140 and 125 kDa were also increasingly detectable, without other more detailed characterization (sequence assignment), during acute hepatitis, whereas no CPS 1 fragments having CPS 1 immunoreactivity were observable in an accompanying immunoblotting analysis in human autopsy samples (Mikiko Ozaki et al., loc. cit.).

Suitability of substantially complete CPS 1 and of soluble CPS 1 fragments, in particular of fragments having molar masses of 68-70 kDa±3 kDa from the N-terminal part of CPS 1, as biomarkers for the diagnosis of inflammations and sepsis in humans, which can be determined in human serum or plasma, is not evident from the literature findings.

Owing to the detected increased formation of human CPS 1 in sepsis, and of fragments of CPS 1 in baboons with experimentally induced sepsis, in particular in contrast to untreated or healthy patients or animals in whose circulation or liver tissue no such fragments were detectable in spite of identical working-up and storage, CPS 1 and its fragments are suitable for diagnostic purposes. If CPS 1 and its fragments are required as reagents or for producing certain specific antibodies for the detection by immunodiagnostic methods known per se, the fragment can be prepared synthetically or by genetic engineering as recombination products by methods which are now part of the prior art.

Furthermore, the required CPS 1 fragments can also be used according to known methods of the modern prior art for producing specific polyclonal or monoclonal antibodies which are suitable as auxiliaries for the diagnostic determination of the peptides according to the invention and/or also as potential therapeutic agents. The production of suitable monoclonal or polyclonal antibodies against known partial peptide sequences is now part of the general prior art.

In the determination of CPS 1 or CPS 1 fragments in patients' sera, it is possible in principle to proceed as described, for example, for the selective procalcitonin determination in P. P. Ghillani et al., "Monoclonal antipeptide antibodies as tools to dissect closely related gene products", The Journal of Immunology, Vol. 141, No. 9, 1988, 3156-3163; and P. P. Ghillani et al., "Identification and Measurement of Calcitonin Precursors in Serum of Patients with Malignant Diseases", Cancer Research, Vol. 49, No. 23, 1989, 6845-6851; reference additionally being made expressly to the immunization techniques described there, which represent one possibility for obtaining monoclonal antibodies also against partial sequences of CPS 1. Variations of the techniques described and/or further immunization techniques can be discovered by a person skilled in the art from relevant standard works and publications and applied in context. A preferred immunoassay for determining CPS 1 in human biological fluids, in particular human serum or plasma, is described below in the experimental section, together with measured results obtained therewith and the more detailed characterization of the analyte detected.

A use of CPS 1 or soluble CPS 1 fragments as a component (reagent) of an assay kit, or a use for producing assay components, for example polyclonal or monoclonal antibodies which are provided, for example, in immobilized and/or marked form as a rule likewise in assay kits, is also to be regarded as a use in the context of the present Application.

The production of CPS 1 antibodies using techniques of direct genetic immunization with DNA should also be expressly mentioned. It is within the scope of the present invention to use, for example, a cDNA of CPS 1 or of the desired CPS 1 fragments for the immunization, since it has been found in the past that the spectrum of obtainable antibodies can be extended by such immunization techniques.

It should additionally expressly be pointed out that, in the determination, according to the invention, of CPS 1 or CPS 1 fragments from the N-terminal part of the CPS 1 sequence, depending on the assay design, any other, for example longer soluble CPS 1 fragments which may be simultaneously present in the biological fluid and contain these fragments, or forms of the complete CPS 1 which are present in soluble form (which is usually localized in the mitochondria) may also be determined or concomitantly determined. In the context of the present invention, such methods too are to be regarded as methods according to the invention for determining CPS 1 or CPS 1 fragments.

CPS 1 according to SEQ ID NO:6 or soluble forms thereof or soluble partial peptides thereof, for example those which contain one of the partial sequences of SEQ ID NO:1 to SEQ ID NO:5 and/or other partial sequences from the N-terminus of CPS 1 or consist thereof, can, on the basis of the present results, therefore serve as specific marker peptides (biomarkers) for diagnosing and monitoring the course of inflammations and infections (in particular, like procalcitonin, also of systemic infections of the sepsis type).

Instead of the determination of CPS 1 or of the CPS 1 fragments or of any posttranslationally modified forms thereof, optionally a determination of the associated mRNA should also not be ruled out for diagnostic purposes. The diagnostic purposes, the CPS 1 determination can be carried out, inter alia, also indirectly as a determination of an enzyme activity, which corresponds to the CPS 1 activity or the residual activity of the CPS 1 fragments.

It is furthermore possible to carry out the determination of CPS 1 and/or CPS 1 fragments as prognosis markers and markers for monitoring the pathological course of inflammations, in particular systemic inflammations, and sepsis as part of a combination measurement with other markers.

In addition to a combination with a procalcitonin measurement, a combination of the measurement of CPS 1 with the determination of other markers for sepsis and systemic inflammation is particularly suitable, in particular with CA 19-9, CA 125, S100B, or S100A proteins involved in the regulation of inflammations, or with the determination of the novel sepsis markers described in the Applicant's prior, unpublished Patent Applications mentioned below, inflammin (DE 101 19 804.3) and CHP (DE 101 31 922.3), and of the protein LASP-1 and/or with the determination of soluble cytokeratin fragments, in particular of the newly discovered soluble cytokeratin-1 fragments (sCY1F; DE 101 30 985.6) and of the known tumour markers CYFRA-21 or TPS and/or of one or more of the above-mentioned prohormones. A simultaneous determination of the known inflammation parameter C-reactive protein (CRP) can also be provided. On the basis of the novel results described in this Application and in the related Applications of the Applicant, a combination with measurements of known biomolecules or biomolecules still to be discovered should also generally be considered for fine diagnosis of sepsis, which biomolecules are suitable as tissue- or organ-specific inflammation markers.

The actual CPS 1 determination can be effected in any suitable manner known per se, immunoassays of a suitable assay design being preferred.

In a preferred embodiment, the immunodiagnostic determination is carried out as a heterogeneous sandwich immunoassay, in which one of the antibodies is immobilized on an arbitrary solid phase, for example the walls of coated test tubes (for example made of polystyrene; "coated tubes"; CT) or on microtitre plates, for example consisting of polystyrene, or in particles, for example magnetic particles, while the other antibody carries a radical which is a directly detectable label or permits select linkage with a label and serves for detection of the sandwich structures formed. Delayed or subsequent immobilization using suitable solid phases is also possible.

In principle, it is possible to use all marking techniques which can be used in assays of the type described, including marking with radio isotopes, enzymes or fluorescent, chemoluminescent or bioluminescent labels and directly optically detectable colour markings, such as, for example, gold atoms and stain particles, as used in particular for point-of-care (POC) or accelerated tests. In the case of heterogeneous sandwich immunoassays, the two antibodies may also have parts of a detection system of the type described below in association with homogeneous assays.

It is therefore within the scope of the present invention to design the method according to the invention also as an accelerated test.

The method according to the invention can furthermore be designed as a homogeneous method in which the sandwich complexes formed from the two antibodies and the CPS 1 to be detected remain suspended in the liquid phase. In such a case, it is preferable to mark both antibodies with parts of a detection system, which then permits generation of signals or triggering of a signal when both antibodies are integrated into a single sandwich. Such techniques should be designed in particular as fluorescence amplification or fluorescence extinction detection methods. A particularly preferred method of this type relates to the use of detection reagents to be employed in pairs, as described, for example, in U.S. Pat. No. 4,822,733, EP-B1-180 492 or EP-B1-539 477 and the prior art cited therein. They permit a measurement which selectively measures only reaction products which contain the two marking components in a single immune complex, directly in the reaction mixture. As an example, reference may be made to the technology offered under the trade names TRACE® (Time Resolved Amplified Cryptate Emission) or KRYPTOR®, which realizes the teachings of the above-mentioned Applications.

The content of said prior Applications of the Applicant is to be regarded as part of the disclosure of the present application through the express reference to these Applications.

Below, the discovery and identification of the CPS 1 fragments and the determination of substances having the immunoreactivity of these fragments in the human circulation, which subsequently proved to be the at least substantially complete enzyme CPS 1 or a soluble form thereof, are described in more detail, reference being made to the attached sequence listing. The figures show the following:

FIG. 1 Views of 2D electrophoresis gels which permit a comparison of the spot pattern of cytoplasmic liver cell proteins of a healthy baboon (A) with the liver cell proteins of a baboon 5 h after a sepsis induced by LPS administration (B). The arrow indicates the positions of the three sepsis-specific products according to the invention (CPS 1 fragments), which are highlighted by a circle in diagram (B).

Figure 2:
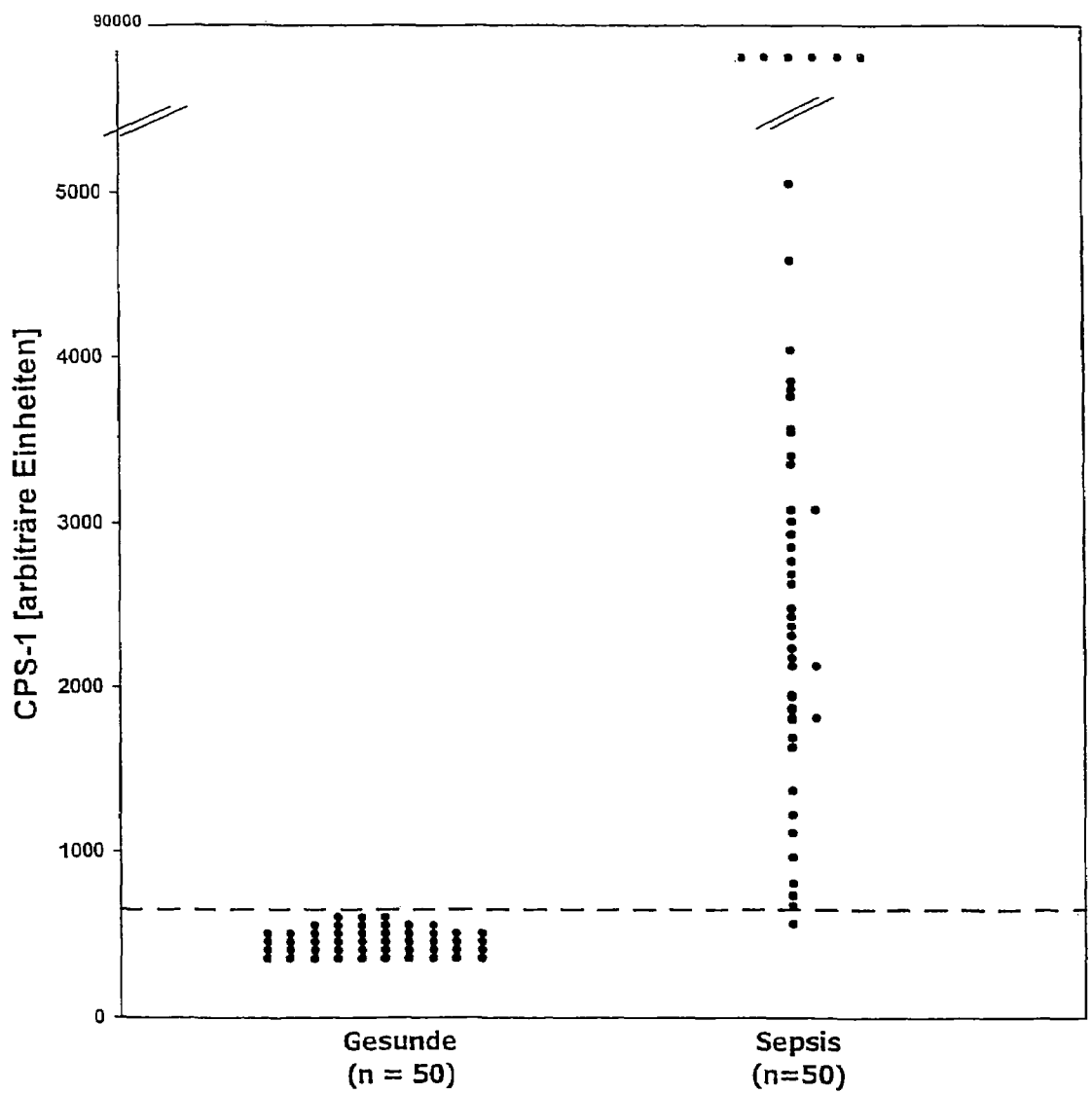

FIG. 2 The results of the measurement of the CPS 1 immunoreactivity in plasmas of healthy normal persons and patients with sepsis by means of an immunoassay described in more detail in the experimental section, the dashed line indicating the lower limit of detection of the test.

Figure 3:
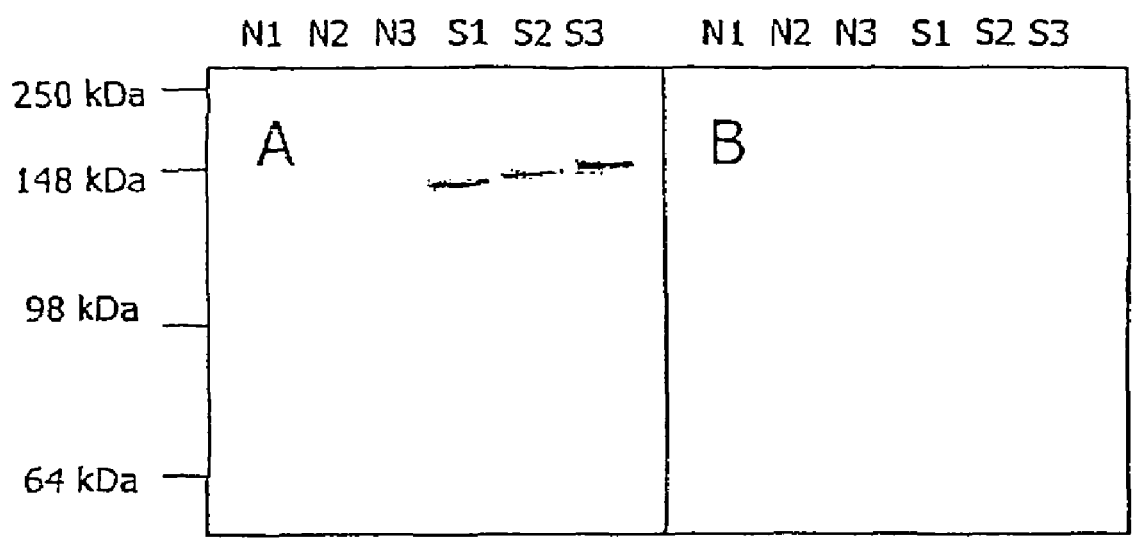

FIG. 3 Western blot bands of plasma samples using anti-CPS antisera. Samples of normal persons (N1-N3) and patients suffering from sepsis (S1-S3) were plotted (panel A). For the detection of CPS 1, a mixture of antisera against two defined CPS 1 epitopes (positions 184-199 and 245-257 of the CPS 1 according to SEQ ID NO:6) was used. The specificity of the reaction was tested by preincubating the antisera, in a second batch (panel B), with an excess of the peptides which had been used for immunizing or obtaining the antisera. The positions of the molecular weight markers are indicated.

Figure 4:
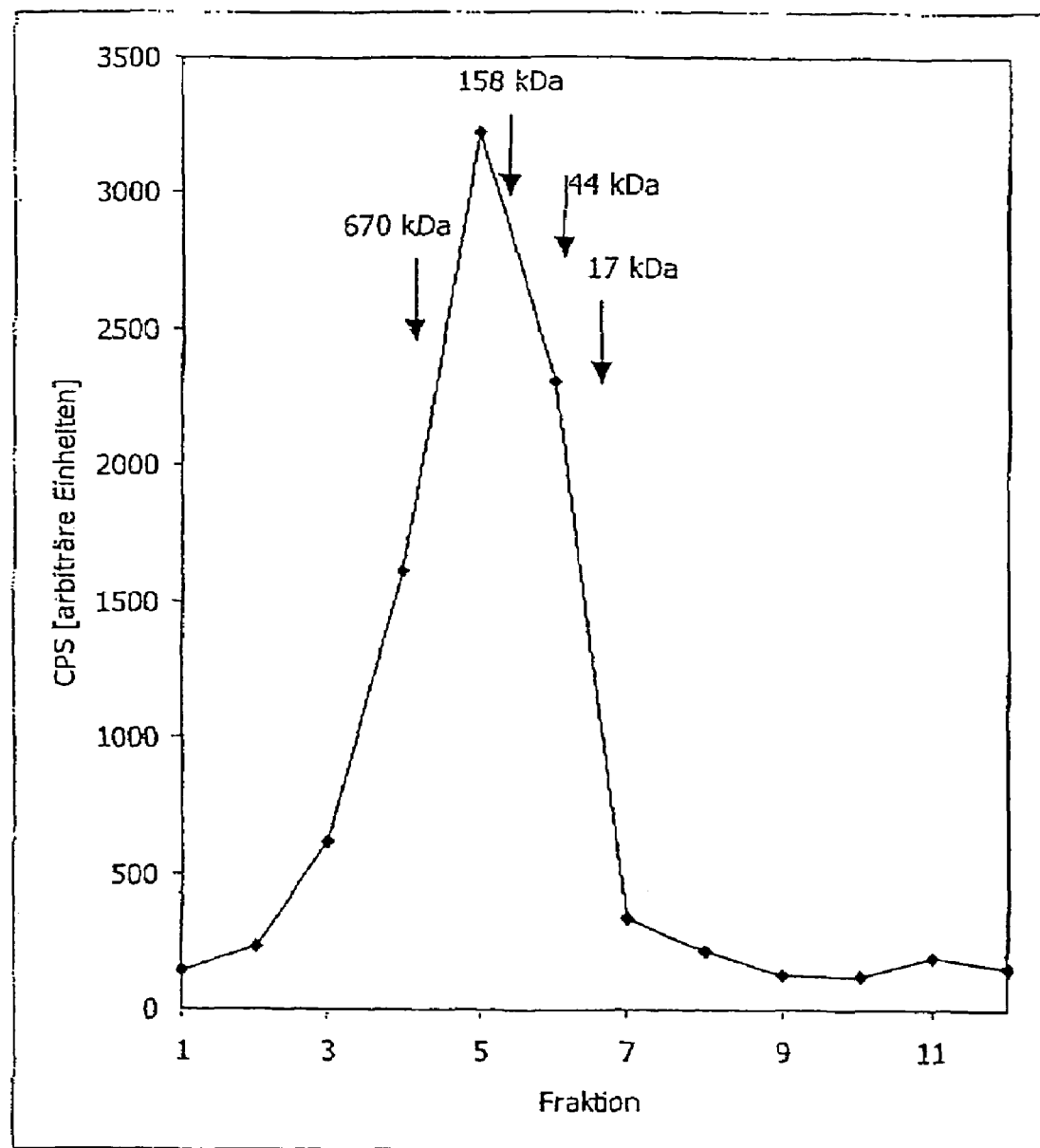

FIG. 4 A CPS 1 immunochromatogram of a gel filtration chromatography of sepsis plasma. 100 µl of a sepsis plasma were chromatographed over a Bio-Sil SEC-400 HPLC column. 1 ml fractions were collected, and the CPS 1 immunoreactivity of the individual fractions was measured. Positions of size standards which were chromatographed in a separate run are shown.

EXPERIMENTAL SECTION

1. Infection Simulation by Endotoxin Administration in an Animal Model (Baboons).

On the basis of the experiments carried out with baboons for the stimulation of procalcitonin secretion by endotoxin injections (cf. H. Redl et al., "Procalcitonin release patterns in a baboon model of trauma and sepsis: Relationship to cytokines and neopterin", Crit Care Med 2000, Vol. 28, No. 11, 3659-3663; H. Redl et al., "Non-Human Primate Models of Sepsis", in: Sepsis 1998; 2:243-253), baboons (male, about 2 years old, weighing from 27 to 29 kg) were each intravenously administered 100 µg of LPS (lipopolysaccharide from *Salmonella Typhimurium*, source: Sigma) per kg body weight. From 5 to 5.5 h after the injection, the animals were sacrificed by intravenous administration of 10 ml of doletal. Within 60 min of their death, all organs/tissues were dissected and were stabilized by freezing in liquid nitrogen.

During the further processing, 1.5 ml of buffer A (50 mM Tris/HCl, pH 7.1, 100 mM KCl, 20% of glycerol) were added to samples of the individual frozen tissues (1 g) while cooling with nitrogen, and the samples were pulverized in a porcelain mortar to give a powder (cf. J. Klose, "Fractionated Extraction of Total Tissue Proteins from Mouse and Human for 2-D Electrophoresis", in: Methods in Molecular Biology, Vol. 112: 2-D Proteome Analysis Protocols, Humana Press Inc., Totowa, N.J.). After subsequent centrifuging for 1 hour at 100,000 g and +4° C., the supernatant obtained was recovered and was stored at −80° C. until required for further processing.

Because experiments with the samples obtained as above had shown that the largest amount of procalcitonin is found in liver tissue of treated animals, protein extracts from the baboon liver were employed in the search for novel sepsis-specific biomarkers.

2. Proteome Analysis using Cytoplasmic Liver Cell Proteins of Baboons.

Cytoplasmic liver cell protein extracts of, on the one hand, healthy baboons (control) and, on the other hand, baboons which had been injected with LPS were used in a proteome analysis. In the initial analytical 2D gel electrophoresis, liver extract containing 100 µg of protein was stabilized to 9M urea, 70 mM DTT, 2% ampholyte pH 2-4 and then separated by means of analytical 2D gel electrophoresis, as described in J. Klose et al., "Two-dimensional electrophoresis of proteins: An updated protocol and implications for a functional analysis of the genome", Electrophoresis 1995, 16, 1034-1059. The visualization of the proteins in the 2D electrophoresis gel was effected by means of silver staining (cf. J. Heukeshoven et al., "Improved silver staining procedure for fast staining in Phast-System Development Unit. I. Staining of sodium dodecyl gels", Electrophoresis 1988, 9, 28-32).

For evaluation, the protein spot patterns of the samples of untreated animals were compared with the protein spot patterns which resulted from liver tissue samples of treated animals. Substances which occurred in no control sample but additionally in all treated animals were selected for further analytical investigations. FIG. 1 shows a comparison of the 2D electrophoresis gels for a control sample (A) and a sample of a treated animal (B), three additional protein spots in (B) having molar masses of approx. 68 kDa, 69 kDa and 70 kDa (±3 kDa) and isoelectric points of approx. 6.0, 5.8 and 5.6 respectively being highlighted by an arrow and a circle.

The novel specific proteins identified in the protein spot pattern of the analytical 2D gel electrophoresis were then prepared by means of preparative 2D gel electrophoresis using 350 µg of protein (once again cf. (10)). In the preparative 2D gel electrophoresis, the staining was effected by means of Coomassie Brilliant Blue G250 (cf. V. Neuhoff et al., "Improved staining of proteins in polyacrylamide gels including isoelectric focusing gels with clear background at nanogram sensitivity using Coomassie Brilliant Blue G-250 and R-250", Electrophoresis 1988, 9, 255-262).

The protein spots preselected for the further analysis were cut out of the gel.

The protein spots were each trypsin-digested using the method which is described in A. Otto et al., "Identification of human myocardial proteins separated by two-dimensional electrophoresis using an effective sample preparation for mass spectrometry", Electrophoresis 1996, 17, 1643-1650, and then analyzed by means of mass spectroscopy, in particular with the use of mass spectrometric investigations as described and discussed, for example in G. Neubauer et al., "Mass spectrometry and EST-database searching allows characterization of the multi-protein spliceosome complex", in: nature genetics, vol. 20, 1998, 46-50; J. Lingner et al., "Reverse Transcriptase Motifs in the Catalytic Subunit of Telomerase", in: Science, Vol. 276, 1997, 561-567; M. Mann et al., "Use of mass spectrometry-derived data to annotate nucleotide and protein sequence databases", in: TRENDS in Biochemical Sciences, Vol. 26, 1, 2001, 54-61.

After an ESI (ElectroSprayIonization), fragments from the trypsin digestion of all three protein spots were also subjected to tandem mass spectrometry. A Q-TOF mass spectrometer having a so-called nanoflow-Z-Spray ion source from Micromass, UK, was used. The procedure corresponded to the working instructions of the equipment manufacturer.

3. Identification of CPS 1 Fragments

As shown in FIGS. 1(A) and 1(B), liver cell extracts of baboons to which an LPS injection had been administered contain, inter alia, three novel protein spots for which molecular weights of approx. 68 kDa, 69 kDa and 70 kDa (±3 kDa) were estimated on the basis of the gel electrophoresis data in comparison with marker substances of known molecular weight, while associated isoelectric points of approx. 6.0, 5.8 and 5.6, respectively, were determined from the relative position of the proteins from the first dimension, i.e. isoelectric points in the range from approx. 5.5 to 6.1.

These proteins were analyzed by mass spectrometry, as explained above.

From the "parent spectra" of the three trypsin-digested proteins, in each case individual fragments ("tags") were identified by tandem mass spectroscopy. The mass spectra obtained for these fragments could be evaluated computationally in a manner known per se and gave the following results (with regard to mass spectroscopy, no distinction is possible between the amino acids leucine (L) and isoleucine (I) and the amino acids lysine (K) and glutamine (Q); the following sequences therefore already take account of the assignment to the known spectrum of complete CPS 1 according to SEQ ID NO:6):

Protein spot at 70 kDa (± 3 kDa):

| Fragment 70/1: | GQNQPVLNITN | (SEQ ID NO:1) |
| Fragment 70/2: | NQPVLNI | (SEQ ID NO:2) |
| Fragment 70/3: | AQTAHIVLEDGTK | (SEQ ID NO:3) |

Protein spot at 69 kDa (± 3 kDa):

| Fragment 69/1: | GQNQPVLNITN | (SEQ ID NO:1) |
| Fragment 69/2: | TAHI | (SEQ ID NO:4) |

Protein spot at 68 kDa (± 3 kDa):

| Fragment 68/1: | NQPVLNI | (SEQ ID NO:2) |
| Fragment 68/2: | AFAMTNQILVEK. | (SEQ ID NO:5) |

The above partial sequences according to SEQ ID NO:1 to SEQ ID NO:5 could be identified as partial sequences of the sequence of human CPS 1, to be found under NiceProt View of SWISS PROT: P31327 and having an amino acid chain with a length of 1500 amino acids and an associated theoretical molar mass (without taking account of any posttranslational modifications) of 164.939 kDa (SEQ ID NO:6). The following assignment of the partial peptides resulted:

SEQ ID NO:1 Amino acids 317-327
SEQ ID NO:2 Amino acids 319-325
SEQ ID NO:4 Amino acids 43-55
SEQ ID NO:5 Amino acids 613-624

The amino acids found span a section from amino acid 43 to amino acid 624, i.e. a substantial part of the amino-terminal part of CPS 1.

It should additionally be pointed out that the sequences found did not enable the related cytosolic enzyme CPS 2 to be assigned.

4. CPS 1 Immunoreactivity Determinations in Human Plasmas of Healthy Normal Persons and Patients Suffering from Sepsis 4.1 Material and Methods 4.1.1. Peptide Syntheses Two ranges were selected (Pos. 184-199: peptide range 1; SEQ ID NO:7; Pos. 245-257: peptide range 2; SEQ ID NO:8), derived from the known amino acid sequence of human CPS 1. In each case supplemented by an N-terminal cysteine residue, both ranges were chemically synthesized as soluble peptides by standard methods, purified, subjected to quality control by means of mass spectrometry and reversed phase HPLC and lyophilized in aliquots (JERINI AG, Berlin, Germany). The amino acid sequences of the peptides are:

```
Peptide PCEN17:    CEFEGQPVDFVDPNKQN      SEQ ID NO:7

Peptide PCVD14:    CVPWNHDFTKMEYD         SEQ ID NO:8
```

Recombinant standard material was obtained from InVivo GmbH (Henningsdorf, Germany). This was a crude cell extract of an *E. coli* strain which expressed the recombinant N-terminal region of human CPS 1 (Pos. 1-640 from SEQ ID NO:6), supplemented by an N-terminal streptag. An arbitrary concentration of CPS 1 was assigned to the extract.

4.1.2. Conjugation and Immunization

By means of MBS (m-maleimidobenzoyl-N-hydroxy-succinimide ester), the above-mentioned peptides PCEN17 and PCVD14 were conjugated with the carrier protein KLH (keyhole limpet hemocyanine) (cf. working instructions "NHS-esters-maleimide crosslinkers" from PIERCE, Rockford, Ill., USA). Sheep were immunized with these conjugates according to the following scheme: each sheep initially received 100 µg of conjugate (stated mass based on the peptide content of the conjugate) and then 50 µg of conjugate every 4 weeks (stated mass based on the peptide content of the conjugate). Beginning with the fourth month after the beginning of the immunization, 700 ml of blood per sheep were taken every 4 weeks and antiserum was obtained therefrom by centrifuging. Conjugations, immunizations and recovery of antisera were carried out by MicroPharm, Carmarthenshire, UK.

4.1.3. Purification of the Antibodies

In a 1-step method, the peptide-specific antibodies were prepared from the antisera which had been obtained beginning with the fourth month after immunization.

For this purpose, the peptides PCEN17 and PCVD14 were first coupled to SulfoLink Gel (cf. working instructions "SulfoLink Kit" from PIERCE, Rockford, Ill., USA). 5 mg of peptide per 5 ml of gel were offered for coupling.

The affinity purification of peptide-specific antibodies from sheep antisera against both peptides was carried out as follows:

The peptide columns were first washed three times alternately with 10 ml each of elution buffer (50 mM citric acid, pH 2.2) and binding buffer (100 mM sodium phosphate, 0.1% Tween, pH 6.8). 100 ml of the antisera were filtered over 0.2 µm, and the column material present was added. For this purpose, the gel was rinsed quantitatively with 10 ml of binding buffer from the column. The incubation was effected overnight at room temperature with swirling. The batches were transferred quantitatively into empty columns (NAP 25, Pharmacia, emptied). The run-throughs were discarded. The material was then washed protein-free (protein content of the wash eluate <0.02 A280 nm) with 250 ml of binding buffer. Elution buffer was added to the washed columns, and 1 ml fractions were collected. The protein content of each fraction was determined by means of the BCA method (cf. working instruction from PIERCE, Rockford, Ill., USA). Fractions having protein concentrations of >0.8 mg/ml were pooled. After protein determination of the pools by means of the BCA method, yields of 27 mg were obtained for the anti-PCEN17 antibody and 33 mg for the anti-PCVD14 antibody.

4.1.4. Marking

500 µl of the purified anti-PCEN17 antibody (see above) in 1 ml of 100 mM potassium phosphate buffer (pH 8.0) were subjected to a buffer change using an NAP-5 gel filtration column (Pharmacia) according to the working instruction. The protein concentration determination of the antibody solution gave a value of 1.5 mg/ml.

For the chemiluminescent marking of the antibody, 10 µl of MA70 acridinium NHS ester (1 mg/ml; HOECHST Behring) were added to 67 µl of the antibody solution and incubated for 15 minutes at room temperature. Thereafter, 423 µl of 1 M glycine were added and incubation was effected for a further 10 minutes. Thereafter, the marking batch was subjected to a buffer change using an NAP-5 gel filtration column (Pharmacia) in 1 ml of mobile phase A (50 mM potassium phosphate, 100 mM NaCl, pH 7.4) according to the working instruction and thereby freed from low molecular weight components. For separating off final residues of labels not bound to antibodies, a gel filtration HPLC was carried out (column: Waters Protein Pak SW300). The sample was applied and was chromatographed at a flow rate of 1 ml/min using mobile phase A. The wavelengths 280 nm and 368 nm were measured using a flow-through photometer. The absorption ratio 368 nm/280 nm as a measure of the degree of marking of the antibody was 0.10 at the peak. The monomeric fractions containing antibodies (retention time 8-10 min) were collected, and were collected in 3 ml of 100 mM sodium phosphate, 150 mM NaCl, 5% bovine serum albumin, 0.1% sodium azide, pH 7.4.

4.1.5. Coupling

Irradiated 5 ml polystyrene tubes (from Greiner) were coated with purified anti-PCVD14 antibody, as follows: the antibody was diluted to a concentration of 6.6 µg/ml in 50 mM Tris, 100 mM NaCl, pH 7.8. 300 µl of this solution were pipetted into each tube. The tubes were incubated for 20 hours at 22° C. The solution was filtered with suction. Each tube was then filled with 4.2 ml of 10 mM sodium phosphate, 2% Karion FP, 0.3% bovine serum albumin, pH 6.5. After 20 hours, the solution was filtered with suction. Finally, the tubes were dried in a vacuum dryer.

4.2. Carrying Out the Immunoassay and Evaluation Thereof 4.2.1. Assay Design

An assay buffer having the following composition was prepared:

100 mM sodium phosphate, 150 mM NaCl, 5% bovine serum albumin, 0.1% unspecific sheep IgG, 0.1% sodium azide, pH 7.4

Recombinant human CPS 1 expressed in *E. coli* and in the form of a crude *E. coli* extract, containing the total soluble intracellular protein, served as standard material. This extract was diluted serially in normal horse serum (from Sigma). The standards thus prepared were assigned arbitrary concentrations according to their dilution.

4.2.2. Measurement of EDTA Plasmas of Apparently Healthy Persons and of Patients Suffering from Sepsis.

50 μl each of standard or sample and 200 μl of assay buffer were pipetted into the above-mentioned test tubes. Incubation was effected for 18 hours at 22° C. with shaking. Washing was then effected 4 times with 1 ml of wash solution (0.1% Tween 20) per tube each time. 200 μl of assay buffer, containing 0.5 million RLU of the MA70 marked tracer antibody, were then pipetted into each tube. Incubation was effected for two hours at 22° C. with shaking. Washing was then effected 4 times with 1 ml of wash solution (0.1% Tween 20) per tube each time, the tube was allowed to drip off and the chemiluminescence bound to the tube was measured in a luminometer (from BERTHOLD, LB952T; base reagents BRAHMS AG).

Using the MultiCalc software (spline fit), the concentration of CPS 1 immunoreactivity was read. The results are shown in FIG. 2. A clear distinction between healthy persons and patients suffering from sepsis is evident.

5. Western Blot Analyses from Plasmas

For the more detailed molecular characterization of the CPS 1 immunoreactivity in sepsis plasmas, samples of such plasmas were analyzed by means of Western Blot:

5.1. Gel Preparation

A 7.5% SDS separation gel for a PROTEAN II xi Cell (from BIO-RAD) was cast according to instructions from Bio-Rad:

11.25 ml of 1 M Tris pH 8.8
+7.5 ml of 30% acrylamide/bisacrylamide (29:1), from Biorad
+10.79 ml of Milli-Q water
+300 μl of 10% SDS
+150 μl of 10% APS
+15 μl of TEMED After covering with a layer of water and polymerization, a 5% SDS collecting gel was cast as follows:

1.25 ml of 1 M Tris pH 6.8
+1.33 ml of 30% acrylamide/bisacrylamide (29:1), from Biorad
+7.26 ml of Milli-Q water
+100 μl of 10% SDS
+50 μl of 10% APS
+10 μl of TEMED 5 ml of collecting gel solution were pipetted onto the separation gel, and the comb was inserted and the solution allowed to polymerize.

5.2. Gel Electrophoresis

20 μl of PBS, 2.5 μl of glycerol and 5 μl of cracking buffer (120 mM Tris/HCl, pH 6.4, 2% SDS, 20% glycerol, 20% β-mercaptoethanol, 0.002% bromophenol blue) were added to 5 μl of EDTA plasma samples from each of three healthy control persons and from each of three patients suffering from sepsis, and incubation was effected for 10 min at 90° C., followed by application. 10 μl of Rainbow Marker RPN 756 (from Pharmacia) were applied as a molecular weight marker.

The chamber used was a PROTEAN II xi Cell (from BIO-RAD). The electrophoresis buffer was: 25 mM Tris/HCl, 90 mM glycine, 0.1% SDS, pH 8.6. The electrophoresis conditions were: 45 min at 46 V/15 mA, 30 min at 120 V/50 mA, 150 min at 150 V/56 mA, 90 min at 190 V/45 mA.

5.3. Blot

The following was used as the blot buffer: 25 mM Tris, 192 mM glycine, 1% SDS, 20% methanol, pH 8.3. The blot film was a Protran BA83 nitrocellulose blot film, 13×13 cm (from Schleicher & Schuell). The blot apparatus was a semi-dry blotter (Pegasus model from Phase).

The gel was incubated for 10 min in blot buffer and placed on the blot film and coated with several layers of Whatman 3 MM chromatography paper (impregnated with blot buffer). Blotting was then effected (0.8 mA/cm$^2$ gel area, 70 min).

5.4. Immune Response:

The blot film was saturated in 150 ml of PBS-Tween-Protein solution (PBS, 0.3% Tween, 1.5% BSA, 50 μg/ml unspecific mouse IgG) overnight at 4° C. with shaking. 30 μl each of sheep anti-PCEN17 and anti-PCVD14 antiserum (for the preparation of the antisera, see above) were then added to the solution, and incubation was effected for 1 h at room temperature with shaking. The solution was decanted, and the blot film was washed for 4×10 min in 300 ml of PBS-Tween-Protein solution each time with shaking. The secondary antibody was then added: 30 μl of monoclonal mouse anti-sheep IgG alkaline phosphatase conjugate (from Sigma, A8062), diluted in 150 ml of PBS-Tween-Protein solution. Incubation was effected for 90 min with shaking at room temperature. Thereafter, decanting was carried out and washing was effected for 10 min with 150 ml of PBS-Tween-Protein solution with shaking. Thereafter, decanting was carried out and washing was effected for 2×10 min with 150 ml of wash buffer (100 mM Tris/HCl, pH 7.5, 150 mM NaCl) with shaking.

Substrate solution was prepared as follows: 100 ml of development buffer (100 mM Tris/HCl, pH 9.5, 100 mM NaCl, 50 mM MgCl$_2$) +350 μl of a solution of 50 mg of BCIP (5-bromo-4-chloro-3-indolyl phosphate, from Sigma) per ml of 100% dimethylformamide, +450 μl of a solution of 100 mg of NBT (nitro blue tetrazolium, from Sigma) per ml of 70% dimethylformamide.

The substrate solution was added to the blot film. After 5 minutes, the colour reaction was stopped by washing the blot film in water. The results are shown in FIG. 3 (panel A).

In a parallel experiment, the corresponding immunogenic peptides PCEN17 and PCVD14, in a final concentration of 2 μg/ml each, were added to the solution containing the primary antisera (sheep anti-PCEN17 or anti-PCVD14 antiserum) and preincubated for 30 min. The results are shown in FIG. 3 (panel B), reference being made expressly to the legend for this FIG. 3.

6. Gel Filtration HPLC of Sepsis Plasma

For the determination of the apparent molecular weight of the CPS 1 immunoreactivity from sepsis plasma in solution, such a plasma was fractionated by means of a gel filtration HPLC and the CPS 1 immunoreactivity in the fractions was measured. The column was calibrated by separate chromatography of standards (Bio-Rad standard: Cat. No. 151-1901). A Bio-Sil SEC-400 column (7.8×300 mm Ser. No. 415949) from Bio-Rad was used. The mobile phase was 300 mM potassium phosphate, 0.1% NaN$_3$, pH 7.0. 100 μl of the sepsis plasma were chromatographed, 1 ml fractions were collected, and 50 μl each thereof were subjected to an immunoassay (for procedure, see above). The results obtained (reactivity/fraction) are shown in FIG. 4, reference expressly being made to the legend for this FIG. 4.

The results of the measurements of the CPS 1 immunoreactivity in human plasmas and of the investigations into the species which was responsible for the immunoreactivity observed may be summarized as follows:

By means of the sandwich immunoassays described, it was shown that plasmas of patients suffering from sepsis have greatly increased concentrations of CPS 1 immunoreactivity, whereas CPS 1 was not detectable in plasmas of healthy persons (FIG. 2).

The CPS 1 immunoreactivity circulating in the sepsis plasmas is evidently substantially the intact enzyme CPS 1 or a form thereof having increased solubility.

Three sepsis plasmas investigated in the Western Blot test showed a specific CPS band at about 150 kDa (FIG. 3). This corresponds approximately to the molecular weight of about 160 kDa, calculated for the intact CPS 1 on the basis of the known amino acid sequence.

The gel filtration HPLC showed that the CPS 1 immunoreactivity of the sepsis plasma investigated has a molecular weight of about 200 kDa (±50 kDa) in solution (FIG. 4).

The measurement of CPS 1 in human serum/plasma has not been described to date, either for patients with sepsis or for other clinical pictures. CPS 1 in plasma was measured only in an experimental rat model for acute hepatitis (see above, Ozaki et al., 1996). However, the conditions in the rat are evidently not comparable with those in humans since, in said publication, CPS concentrations of 1-2 µg/ml were detected even for healthy animals, whereas the herein-described measurements of human plasmas of healthy persons by the Applicant gave values below the limit of detection (estimated at about 0.5 ng/ml).

Surprisingly, a considerable increase in the CPS 1 immunoreactivity in plasma was found for patients suffering from sepsis. It is known that damage to the mitochondria occurs in the case of sepsis (Crouser ED et al., Endotoxin-induced mitochondrial damage correlates with impaired respiratory activity; Crit Care Med February 2002; 30(2):276-84). Such damage in combination with necrosis or apoptosis might be the cause of the transfer of CPS 1 from the mitochondrial matrix into the blood circulation. Since CPS 1 is expressed virtually exclusively in the liver and accounts there for a considerable part of the total soluble protein, the measurement of CPS 1 might be particularly suitable for indicating damage to the liver in the case of severe sepsis or in other contexts, for example in the case of multiorgan failure.

Apart from a determination in connection with diagnosis, monitoring or prognosis of sepsis generally, the determination of CPS 1 or CPS 1 immunoreactivity can therefore be carried out in particular also for diagnosis, monitoring or prognosis of liver failure in the case of multiorgan failure or for determinations in connection with inflammatory and other liver diseases.

The discoveries on which the present invention is based and relating to the occurrence of considerable concentrations of CPS 1 in the circulation of patients suffering from severe diseases, such as sepsis and severe liver diseases, make it appear possible that CPS 1, also in dissolved form, has retained at least parts of an enzyme reactivity and contributes to a worsening of the disease and/or to certain undesired pathological consequences. This shows that substances known per se which inhibit the expression or the enzymatic action of CPS 1 may be suitable for positively influencing the pathological process. Such substances are described, for example, in J Steroid Biochem Mol Bio May 1991; 38(5): 599-609; J Biol Chem May 1977 25; 252(10):3558-60; J Biol Chem January 1984 10; 259(1):323-31 and J Biol Chem November 1981 10; 256(21):11160-5; J Biol Chem April 1981 10; 256(7):3443-6. They include in particular Ca ions and other metal ions and substances of the steroid type.

The invention claimed is:

1. A method for the diagnosis of sepsis in a human patient comprising:
   (a) obtaining a blood, plasma, or serum sample from said patient; and
   determining the presence and amount of human carbamoyl phosphate synthetase 1 (CPS 1) (SEQ ID NO: 6) in said sample using an immunodiagnostic assay.

2. The method of claim 1, further comprising determining the presence and amount of:
   (a) human CPS 1 (SEQ ID NO:6) having an apparent molecular weight of 200 kDa +/−50 kDa using gel filtration and HPLC;
   fragments of human CPS 1 (SEQ ID NO:6) having an apparent molecular weight of 68 to 70 kDa+/−3kDa; and isoelectric points in the range from 5.5 to 6.1 in said sample using two-dimensional gel electrophoresis.

3. The method of claim 1, wherein the immunodiagnostic assay is a sandwich assay.

4. The method according to claim 1, wherein said method comprises using one or more antibody that specifically recognizes the N-terminal portion of human CPS 1 consisting of amino acids 1-630 of SEQ ID NO:6.

5. The method according to claim 4, wherein the one or more antibody binds a sequence chosen from SEQ ID NO.: 1, SEQ ID NO.:2, SEQ ID NO.:3, SEQ ID NO.:4, SEQ ID NO.:5, SEQ ID NO.:7 and SEQ ID NO.:8.

6. The method of claim 5, wherein the antibodies are produced from a protein chosen from SEQ ID NO:7 and SEQ ID NO:8.

7. The method according to claim 1, wherein step (b) alternatively comprises: performing a multi-parameter determination, wherein the presence and amount of human carbamoyl phosphate synthetase 1 (CPS 1) (SEQ ID NO:6) is co-determined with at least one other sepsis marker.

8. The method according to claim 7, wherein the at least one other sepsis marker is chosen from procalcitonin, cancer antigen 19-9 (CA 19-9), cancer antigen 125 (CA 125), protein S100B, protein S100 A, soluble cytokeratin fragments, inflammin peptide, calcitonin-homologue peptide (CHP), the LIM, actin, and SH3 domain protein-1 (LASP-1), peptide prohormone immunoreactivity, and C-reactive protein (CRP).

9. The method of claim 8, wherein the soluble cytokeratin fragments are chosen from soluble cytokeratin-19 fragments (CYFRA 21), a soluble cytokeratin-18 fragment known as polypeptide specific antigen (TPS), and soluble cytokeratin-1 fragments (sCY1 F).

10. The method according to claim 7, wherein the multi-parameter determination is carried out as a simultaneous determination by means of a chip technology measuring device or of an immunochromatographic measuring device.

11. The method according to claim 10, wherein said measuring device provides a complex measured result that is evaluated with the aid of a computer program.

12. The method of claim 1 further comprising determining the severity of sepsis on the basis of the concentration of CPS 1, wherein the greater the concentration of CPS 1, the greater the severity of sepsis.

* * * * *

UNITED STATES PATENT AND TRADEMARK OFFICE
CERTIFICATE OF CORRECTION

PATENT NO.         : 7,413,850 B2                                        Page 1 of 1
APPLICATION NO.    : 10/511756
DATED              : August 19, 2008
INVENTOR(S)        : Bergmann et al.

It is certified that error appears in the above-identified patent and that said Letters Patent is hereby corrected as shown below:

Title Page, Item (54) and Col. 1

In The Title:

Delete "FOR THE DIAGNOIS OF" and insert -- FOR THE DIAGNOSIS OF --

In The Claims:

Claim 2, Col. 25, Line 32: Delete "comprising detennining" and insert -- comprising determining --

Claim 2, Col. 25, Line 37: Delete "fragments of human" and insert -- (b) fragments of human --

Claim 2, Col. 25, Line 40: Delete "gel electrophoresis." and insert -- gel electrophoresis, wherein an elevated concentration of human CPS 1, or said fragments or components thereof, in indicative of sepsis. --

Signed and Sealed this

Twenty-third Day of March, 2010

David J. Kappos
*Director of the United States Patent and Trademark Office*

SEQUENCE LISTING

```
<160> NUMBER OF SEQ ID NOS: 8

<210> SEQ ID NO 1
<211> LENGTH: 11
<212> TYPE: PRT
<213> ORGANISM: Homo sapiens

<400> SEQUENCE: 1

Gly Gln Asn Gln Pro Val Leu Asn Ile Thr Asn
 1               5                  10

<210> SEQ ID NO 2
<211> LENGTH: 7
<212> TYPE: PRT
<213> ORGANISM: Homo sapiens

<400> SEQUENCE: 2

Asn Gln Pro Val Leu Asn Ile
 1               5

<210> SEQ ID NO 3
<211> LENGTH: 13
<212> TYPE: PRT
<213> ORGANISM: Homo sapiens

<400> SEQUENCE: 3

Ala Gln Thr Ala His Ile Val Leu Glu Asp Gly Thr Lys
 1               5                  10

<210> SEQ ID NO 4
<211> LENGTH: 4
```

```
<212> TYPE: PRT
<213> ORGANISM: Homo sapiens

<400> SEQUENCE: 4

Thr Ala His Ile
  1

<210> SEQ ID NO 5
<211> LENGTH: 12
<212> TYPE: PRT
<213> ORGANISM: Homo sapiens

<400> SEQUENCE: 5

Ala Phe Ala Met Thr Asn Gln Ile Leu Val Glu Lys
  1               5                  10

<210> SEQ ID NO 6
<211> LENGTH: 1500
<212> TYPE: PRT
<213> ORGANISM: Homo sapiens

<400> SEQUENCE: 6

Met Thr Arg Ile Leu Thr Ala Phe Lys Val Val Arg Thr Leu Lys Thr
  1               5                  10                  15

Gly Phe Gly Phe Thr Asn Val Thr Ala His Gln Lys Trp Lys Phe Ser
                 20                  25                  30

Arg Pro Gly Ile Arg Leu Leu Ser Val Lys Ala Gln Thr Ala His Ile
             35                  40                  45

Val Leu Glu Asp Gly Thr Lys Met Lys Gly Tyr Ser Phe Gly His Pro
 50                  55                  60

Ser Ser Val Ala Gly Glu Val Val Phe Asn Thr Gly Leu Gly Gly Tyr
 65                  70                  75                  80

Pro Glu Ala Ile Thr Asp Pro Ala Tyr Lys Gly Gln Ile Leu Thr Met
                 85                  90                  95

Ala Asn Pro Ile Ile Gly Asn Gly Gly Ala Pro Asp Thr Thr Ala Leu
            100                 105                 110

Asp Glu Leu Gly Leu Ser Lys Tyr Leu Glu Ser Asn Gly Ile Lys Val
            115                 120                 125

Ser Gly Leu Leu Val Leu Asp Tyr Ser Lys Asp Tyr Asn His Trp Leu
        130                 135                 140

Ala Thr Lys Ser Leu Gly Gln Trp Leu Gln Glu Lys Val Pro Ala
145                 150                 155                 160

Ile Tyr Gly Val Asp Thr Arg Met Leu Thr Lys Ile Ile Arg Asp Lys
                165                 170                 175

Gly Thr Met Leu Gly Lys Ile Glu Phe Glu Gly Gln Pro Val Asp Phe
            180                 185                 190

Val Asp Pro Asn Lys Gln Asn Leu Ile Ala Glu Val Ser Thr Lys Asp
        195                 200                 205

Val Lys Val Tyr Gly Lys Gly Asn Pro Thr Lys Val Val Ala Val Asp
    210                 215                 220

Cys Gly Ile Lys Asn Asn Val Ile Arg Leu Leu Val Lys Arg Gly Ala
225                 230                 235                 240

Glu Val His Leu Val Pro Trp Asn His Asp Phe Thr Lys Met Glu Tyr
                245                 250                 255

Asp Gly Ile Leu Ile Ala Gly Gly Pro Gly Asn Pro Ala Leu Ala Glu
            260                 265                 270

Pro Leu Ile Gln Asn Val Arg Lys Ile Leu Glu Ser Asp Arg Lys Glu
```

-continued

```
                275                 280                 285
Pro Leu Phe Gly Ile Ser Thr Gly Asn Leu Ile Thr Gly Leu Ala Ala
290                     295                 300
Gly Ala Lys Thr Tyr Lys Met Ser Met Ala Asn Arg Gly Gln Asn Gln
305                 310                 315                 320
Pro Val Leu Asn Ile Thr Asn Lys Gln Ala Phe Ile Thr Ala Gln Asn
                325                 330                 335
His Gly Tyr Ala Leu Asp Asn Thr Leu Pro Ala Gly Trp Lys Pro Leu
                340                 345                 350
Phe Val Asn Val Asn Asp Gln Thr Asn Glu Gly Ile Met His Glu Ser
                355                 360                 365
Lys Pro Phe Phe Ala Val Gln Phe His Pro Glu Val Thr Pro Gly Pro
370                 375                 380
Ile Asp Thr Glu Tyr Leu Phe Asp Ser Phe Phe Ser Leu Ile Lys Lys
385                 390                 395                 400
Gly Lys Ala Thr Thr Ile Thr Ser Val Leu Pro Lys Pro Ala Leu Val
                405                 410                 415
Ala Ser Arg Val Glu Val Ser Lys Val Leu Ile Leu Gly Ser Gly Gly
                420                 425                 430
Leu Ser Ile Gly Gln Ala Gly Glu Phe Asp Tyr Ser Gly Ser Gln Ala
                435                 440                 445
Val Lys Ala Met Lys Glu Glu Asn Val Lys Thr Val Leu Met Asn Pro
                450                 455                 460
Asn Ile Ala Ser Val Gln Thr Asn Glu Val Gly Leu Lys Gln Ala Asp
465                 470                 475                 480
Thr Val Tyr Phe Leu Pro Ile Thr Pro Gln Phe Val Thr Glu Val Ile
                485                 490                 495
Lys Ala Glu Gln Pro Asp Gly Leu Ile Leu Gly Met Gly Gly Gln Thr
                500                 505                 510
Ala Leu Asn Cys Gly Val Glu Leu Phe Lys Arg Gly Val Leu Lys Glu
                515                 520                 525
Tyr Gly Val Lys Val Leu Gly Thr Ser Val Glu Ser Ile Met Ala Thr
530                     535                 540
Glu Asp Arg Gln Leu Phe Ser Asp Lys Leu Asn Glu Ile Asn Glu Lys
545                 550                 555                 560
Ile Ala Pro Ser Phe Ala Val Glu Ser Ile Glu Asp Ala Leu Lys Ala
                565                 570                 575
Ala Asp Thr Ile Gly Tyr Pro Val Met Ile Arg Ser Ala Tyr Ala Leu
                580                 585                 590
Gly Gly Leu Gly Ser Gly Ile Cys Pro Asn Arg Glu Thr Leu Met Asp
                595                 600                 605
Leu Ser Thr Lys Ala Phe Ala Met Thr Asn Gln Ile Leu Val Glu Lys
                610                 615                 620
Ser Val Thr Gly Trp Lys Glu Ile Glu Tyr Glu Val Val Arg Asp Ala
625                 630                 635                 640
Asp Asp Asn Cys Val Thr Val Cys Asn Met Glu Asn Val Asp Ala Met
                645                 650                 655
Gly Val His Thr Gly Asp Ser Val Val Val Ala Pro Ala Gln Thr Leu
                660                 665                 670
Ser Asn Ala Glu Phe Gln Met Leu Arg Arg Thr Ser Ile Asn Val Val
                675                 680                 685
Arg His Leu Gly Ile Val Gly Glu Cys Asn Ile Gln Phe Ala Leu His
                690                 695                 700
```

```
Pro Thr Ser Met Glu Tyr Cys Ile Ile Glu Val Asn Ala Arg Leu Ser
705                 710                 715                 720

Arg Ser Ser Ala Leu Ala Ser Lys Ala Thr Gly Tyr Pro Leu Ala Phe
            725                 730                 735

Ile Ala Ala Lys Ile Ala Leu Gly Ile Pro Leu Pro Glu Ile Lys Asn
                740                 745                 750

Val Val Ser Gly Lys Thr Ser Ala Cys Phe Glu Pro Ser Leu Asp Tyr
            755                 760                 765

Met Val Thr Lys Ile Pro Arg Trp Asp Leu Asp Arg Phe His Gly Thr
    770                 775                 780

Ser Ser Arg Ile Gly Ser Ser Met Lys Ser Val Gly Glu Val Met Ala
785                 790                 795                 800

Ile Gly Arg Thr Phe Glu Glu Ser Phe Gln Lys Ala Leu Arg Met Cys
                805                 810                 815

His Pro Ser Ile Glu Gly Phe Thr Pro Arg Leu Pro Met Asn Lys Glu
            820                 825                 830

Trp Pro Ser Asn Leu Asp Leu Arg Lys Glu Leu Ser Glu Pro Ser Ser
            835                 840                 845

Thr Arg Ile Tyr Ala Ile Ala Lys Ala Ile Asp Asp Asn Met Ser Leu
    850                 855                 860

Asp Glu Ile Glu Lys Leu Thr Tyr Ile Asp Lys Trp Phe Leu Tyr Lys
865                 870                 875                 880

Met Arg Asp Ile Leu Asn Met Glu Lys Thr Leu Lys Gly Leu Asn Ser
                885                 890                 895

Glu Ser Met Thr Glu Thr Leu Lys Arg Ala Lys Glu Ile Gly Phe
            900                 905                 910

Ser Asp Lys Gln Ile Ser Lys Cys Leu Gly Leu Thr Glu Ala Gln Thr
    915                 920                 925

Arg Glu Leu Arg Leu Lys Lys Asn Ile His Pro Trp Val Lys Gln Ile
930                 935                 940

Asp Thr Leu Ala Ala Glu Tyr Pro Ser Val Thr Asn Tyr Leu Tyr Val
945                 950                 955                 960

Thr Tyr Asn Gly Gln Glu His Asp Val Asn Phe Asp His Gly Met
            965                 970                 975

Met Val Leu Gly Cys Gly Pro Tyr His Ile Gly Ser Ser Val Glu Phe
            980                 985                 990

Asp Trp Cys Ala Val Ser Ser Ile Arg Thr Leu Arg Gln Leu Gly Lys
    995                 1000                1005

Lys Thr Val Val Val Asn Cys Asn Pro Glu Thr Val Ser Thr Asp Phe
    1010                1015                1020

Asp Glu Cys Asp Lys Leu Tyr Phe Glu Glu Leu Ser Leu Glu Arg Ile
1025                1030                1035                1040

Leu Asp Ile Tyr His Gln Glu Ala Cys Gly Gly Cys Ile Ile Ser Val
            1045                1050                1055

Gly Gly Gln Ile Pro Asn Asn Leu Ala Val Pro Leu Tyr Lys Asn Gly
        1060                1065                1070

Val Lys Ile Met Gly Thr Ser Pro Leu Gln Ile Asp Arg Ala Glu Asp
    1075                1080                1085

Arg Ser Ile Phe Ser Ala Val Leu Asp Glu Leu Lys Val Ala Gln Ala
    1090                1095                1100

Pro Trp Lys Ala Val Asn Thr Leu Asn Glu Ala Leu Glu Phe Ala Lys
1105                1110                1115                1120
```

Ser Val Asp Tyr Pro Cys Leu Leu Arg Pro Ser Tyr Val Leu Ser Gly
         1125                1130                1135

Ser Ala Met Asn Val Val Phe Ser Glu Asp Glu Met Lys Lys Phe Leu
         1140                1145                1150

Glu Glu Ala Thr Arg Val Ser Gln Glu His Pro Val Val Leu Thr Lys
         1155                1160                1165

Phe Val Glu Gly Ala Arg Glu Val Glu Met Asp Ala Val Gly Lys Asp
    1170                1175                1180

Gly Arg Val Ile Ser His Ala Ile Ser Glu His Val Glu Asp Ala Gly
1185                1190                1195                1200

Val His Ser Gly Asp Ala Thr Leu Met Leu Pro Thr Gln Thr Ile Ser
         1205                1210                1215

Gln Gly Ala Ile Glu Lys Val Lys Asp Ala Thr Arg Lys Ile Ala Lys
         1220                1225                1230

Ala Phe Ala Ile Ser Gly Pro Phe Asn Val Gln Phe Leu Val Lys Gly
         1235                1240                1245

Asn Asp Val Leu Val Ile Glu Cys Asn Leu Arg Ala Ser Arg Ser Phe
    1250                1255                1260

Pro Phe Val Ser Lys Thr Leu Gly Val Asp Phe Ile Asp Val Ala Thr
1265                1270                1275                1280

Lys Val Met Ile Gly Glu Asn Val Asp Glu Lys His Leu Pro Thr Leu
         1285                1290                1295

Asp His Pro Ile Ile Pro Ala Asp Tyr Val Ala Ile Lys Ala Pro Met
         1300                1305                1310

Phe Ser Trp Pro Arg Leu Arg Asp Ala Asp Pro Ile Leu Arg Cys Glu
         1315                1320                1325

Met Ala Ser Thr Gly Glu Val Ala Cys Phe Gly Glu Gly Ile His Thr
    1330                1335                1340

Ala Phe Leu Lys Ala Met Leu Ser Thr Gly Phe Lys Ile Pro Gln Lys
1345                1350                1355                1360

Gly Ile Leu Ile Gly Ile Gln Gln Ser Phe Arg Pro Arg Phe Leu Gly
         1365                1370                1375

Val Ala Glu Gln Leu His Asn Glu Gly Phe Lys Leu Phe Ala Thr Glu
         1380                1385                1390

Ala Thr Ser Asp Trp Leu Asn Ala Asn Asn Val Pro Ala Thr Pro Val
         1395                1400                1405

Ala Trp Pro Ser Gln Glu Gly Gln Asn Pro Ser Leu Ser Ser Ile Arg
    1410                1415                1420

Lys Leu Ile Arg Asp Gly Ser Ile Asp Leu Val Ile Asn Leu Pro Asn
1425                1430                1435                1440

Asn Asn Thr Lys Phe Val His Asp Asn Tyr Val Ile Arg Arg Thr Ala
         1445                1450                1455

Val Asp Ser Gly Ile Pro Leu Leu Thr Asn Phe Gln Val Thr Lys Leu
         1460                1465                1470

Phe Ala Glu Ala Val Gln Lys Ser Arg Lys Val Asp Ser Lys Ser Leu
         1475                1480                1485

Phe His Tyr Arg Gln Tyr Ser Ala Gly Lys Ala Ala
         1490                1495                1500

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic -continued

```
peptide

<400> SEQUENCE: 7

Cys Glu Phe Glu Gly Gln Pro Val Asp Phe Val Asp Pro Asn Lys Gln
  1               5                   10                  15

Asn

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Val Pro Trp Asn His Asp Phe Thr Lys Met Glu Tyr Asp
  1               5                   10
```